United States Patent
Naritake et al.

(10) Patent No.: US 8,701,730 B2
(45) Date of Patent: Apr. 22, 2014

(54) DEVICE FOR STICKING COVER GLASS

(75) Inventors: Kohji Naritake, Chikuma (JP);
Kiyokazu Iijima, Chikuma (JP); Seiichi Takizawa, Chikuma (JP); Tetsu Nagabayashi, Chikuma (JP)

(73) Assignees: Sakura Seiki Co., Ltd., Nagano (JP);
Sakura Finetek Japan Co., Ltd., Tokyo (JP)

( * ) Notice: Subject to any disclaimer, the term of this patent is extended or adjusted under 35 U.S.C. 154(b) by 238 days.

(21) Appl. No.: 12/937,238

(22) PCT Filed: Apr. 21, 2009

(86) PCT No.: PCT/JP2009/057907
§ 371 (c)(1),
(2), (4) Date: Oct. 8, 2010

(87) PCT Pub. No.: WO2009/131112
PCT Pub. Date: Oct. 29, 2009

(65) Prior Publication Data
US 2011/0032610 A1    Feb. 10, 2011

(30) Foreign Application Priority Data
Apr. 22, 2008  (JP) ................................. 2008-111775

(51) Int. Cl.
*B32B 41/00* (2006.01)

(52) U.S. Cl.
USPC ............. 156/356; 156/360; 156/378; 422/63; 422/65; 422/105

(58) Field of Classification Search
USPC ......... 156/64, 378, 356, 360; 422/63, 65, 105
See application file for complete search history.

(56) References Cited

U.S. PATENT DOCUMENTS

2007/0151672 A1* 7/2007 Takahashi et al. ............ 156/516

FOREIGN PATENT DOCUMENTS

JP    5961868    4/1984
(Continued)

OTHER PUBLICATIONS

International Search Report dated Jul. 7, 2009 for PCT/JP2009/057907.

*Primary Examiner* — George Koch
(74) *Attorney, Agent, or Firm* — Blakely Sokoloff Taylor & Zafman LLP

(57) ABSTRACT

Problems of a conventional cover glass sticking device, in which a slide glass having one end side, where a describing portion is formed, is stored in a storage container and the one end side is always projected from level of a protection liquid therein, are solved by the device of the present invention. The device sticks a cover glass onto a sample applied to a slide glass 12 having one end side, where a describing portion is formed, with an enclosure agent, the device comprises: a basket 22 into which the plurality of slide glasses 12 are inserted; a storage container 20 for immersing the basket in a protection liquid, which protects samples on the slide glasses 12, so as to immerse the entire slide glasses 12 therein; a lifting/feeding unit 36 for lifting the basket 22 to project one end side of the slide glass 12 from the level of the protection liquid and feeding the baskets 22 sequentially to a position of a detection sensor 42 for detecting the position of one end side of the slide glass 12 projecting from the protection liquid; a take-out unit 24 for holding a side face of one end side of the slide glass 12, which has been detected by the detection sensor 42, and taking out the slide glass 12 from the protection liquid; and a cage 34 for containing the slide glass 12, on which the cover glass has been stuck to cover the sample.

8 Claims, 10 Drawing Sheets

(56) References Cited

FOREIGN PATENT DOCUMENTS

| | | |
|---|---|---|
| JP | U60170321 | 4/1984 |
| JP | 2001027731 | 1/2001 |
| JP | 2005221493 | 8/2005 |
| JP | 2005300323 | 10/2005 |

\* cited by examiner

DEVICE FOR STICKING COVER GLASS

CROSS-REFERENCE TO RELATED APPLICATION

This is a non-provisional application claiming the benefit of International Patent Application No. PCT/JP2009/057907, filed Apr. 21, 2009.

FIELD OF TECHNOLOGY

The present invention relates to a device for sticking a cover glass.

BACKGROUND TECHNOLOGY

A microscopic specimen, e.g., a tissue sample cut from an affected part of a patient, is produced, as shown in FIG. 11, by the steps of: applying a sliced tissue sample 10 onto one side face of a slide glass 12; degreasing and staining the sample; dispensing an enclosure agent 14 onto the sample 10 applied on the slide glass 12; and mounting a cover glass 16 onto the enclosure agent 14. After that, a solvent included in the enclosure agent evaporates, so that the enclosure agent solidifies and the cover glass is fixed thereon. Automatization of the process of producing a microscopic specimen has been strongly required by, for example, medical experts who produce a lot of microscopic specimens in a short time.

A conventional cover glass sticking device, which is shown in FIG. 12, is disclosed in Patent Document 1 described later.

In the cover glass sticking device shown in FIG. 12, a protection liquid, e.g., xylene, is stored in a storage container 100 shown in FIG. 13, slide glasses 12, on which specimen samples are respectively applied, are inserted in baskets 102, 102 . . . and immersed in the protection liquid, and the slide glass 12 is transferred to a position 112, which is located at one end of a conveying unit 110, by a rotatable sucking member 106.

The slide glass 12 located at the position 112 is conveyed to a position 114, by the conveying unit 110, so as to dispense an enclosure agent, by a dispenser 119, onto the specimen sample applied on the slide glass 12.

The slide glass 12, on which the enclosure agent has been dispensed, is conveyed to a position 116, by the conveying unit, so as to mount an uppermost cover glass 16 of stacked cover glasses 16, 16 . . . , by a mounting unit, onto the enclosure agent.

Next, the slide glass 12, on which the cover glass 16 has been mounted, is conveyed to a position 118, which is located at the other end of the conveying unit 110 and accommodated in a rack (not shown).

Patent Document 1: Japanese Laid-open Patent Publication No. 2001-27731

DISCLOSURE OF THE INVENTION

By employing the cover glass sticking device shown in FIGS. 12 and 13, the steps for sticking the cover glass, which are included in the process of producing a microscopic specimen, can be automatized, so that the time required for producing a microscopic specimen can be made shorter than ever before.

The cover glass sticking device is automatically operated without an operator, so it is impossible to check if the sample 10 applied on the slide glass 12 in the storage container 100 is projected from the protection liquid or not. Thus, it is required to immerse the entire slide glass 12 in the protection liquid stored in the storage container 100 so as to securely prevent the sample 10 applied on the slide glass 12 from being dried and stick the cover glass on the sample.

However, in the cover glass sticking device shown in FIGS. 12 and 13, the sucking member 106 of the take-out unit 108 must sucks the one end side of the slide glass 12.

On the other hand, in a state where the entire slide glass is immersed in the protection liquid, the sucking member 106 cannot suck the slide glass. Thus, the one end side of the slide glass 12 must be projected from the protection liquid so as to suck the slide glass 12 immersed in the slide glass 12 by the sucking member 106.

A describing portion 18, where letters or symbols indicating a prescribed item(s) of the sample 10 are written, is usually provided to the one end side of the slide glass 12 as shown in FIG. 14. In a state where the sucking member 106 sucks the one end side of the slide glass 12, the sucking member 106 sucks a part of the describing portion 18 as shown in FIG. 15.

However, even if the one end side of the slide glass 12 including the describing portion 18 is projected from the protection liquid when the slide glass 12 which has been entirely immersed in the protection liquid is sucked by the sucking member 106, the protection liquid remains on the describing portion 18.

If the sucking member 106 sucks the describing portion 18 on which the protection liquid has remained, the letters or marks written on the describing portion 18 will be blurred and they cannot be read.

Further, if the protection liquid remaining on the sucking member 106 is mixed with the enclosure agent on the sample 10, the sticking strength of the cover glass 16 will be worsened.

Therefore, in the conventional cover glass sticking device shown in FIGS. 12 and 13, the one end side of the slide glass 12, where the describing portion is formed, must be always projected from the level of the protection liquid stored in the storage container 100, so it is difficult to store the slide glass 12 in the state where the entire slide glass 12 is immersed in the protection liquid stored in the storage container 100.

An object of the present invention is to provide a device for sticking a cover glass which is capable of: solving the problems of the conventional cover glass sticking device, in which the one end side of the slide glass, where the describing portion is formed, must be always projected from the level of the protection liquid stored in the storage container; storing the slide glass having one end side, where a describing portion is formed, in a storage container, in a state where the entire slide glass is immersed in the protection liquid; and preventing letters or marks written in the describing portion from being blurred.

The inventors of the present invention have studied to achieve the object, and they found that the slide glass could be taken out, without take-out means contacting the describing portion which was formed on one side face of the one end side of the slide glass, from the protection liquid by holding the other side face of the one end side of the slide glass, where no describing portion is formed, with the take-out means, and that blur of letters or marks written in the describing portion, which was caused by contact between the take-out means and the describing portion formed on the one side face of the one end side of the slide glass, could be prevented by said manner.

Further, the take-out means could securely hold the slide glass by projecting the one end side of the slide glass from the protection liquid immediately before taking out the slide glass.

As described above, remaining the protection liquid on the describing portion could be prevented by projecting the one end side of the slide glass form the protection liquid.

The inventors further found that extending the enclosure agent, which has been dispensed on the sample applied on the one side face of the slide glass, to the describing portion could be prevented.

Namely, to achieve the object, the device of the present invention sticks a cover glass to a sample of microscopic specimen applied to a slide glass having one end side, where a describing portion is formed on one side face, with an enclosure agent, and the device comprises: a storage container for immersing a basket, into which the plurality of slide glasses have been inserted, in a protection liquid, which is stored in the storage container and which protects samples of microscopic specimen applied on the slide glasses, so as to immerse the entire slide glasses therein; means for lifting the basket to project one end side of the slide glass from the level of the protection liquid; means for feeding the basket sequentially to a position of a detection sensor for detecting the position of one end side of the slide glass projecting from the protection liquid; take-out means for holding a side face of one end side of the slide glass, which has been detected by the detection sensor, and taking out the slide glass from the protection liquid; and a cage for containing the slide glass, on which the cover glass has been stuck to cover the sample.

Preferred modifications of the present invention will be explained.

The device may further comprise means for conveying a vacant basket, from which all of the slide glasses have been taken out, to a vacant basket accommodating section, and thereby the vacant basket can be removed from the storage container, and the slide glass in the next basket can be easily taken out.

The plurality of cages may be used and the slide glasses in one basket may be contained in the same cage, and thereby the slide glasses fed and the slide glasses on which the cover glasses have been stuck can be easily confirmed.

The lifting means and the feeding means may be integrated, and thereby the device for sticking a cover glass can be downsized.

EFFECTS OF THE INVENTION

In the device of the present invention, the basket, in which the slide glasses are inserted, is immersed in the protection liquid stored in the storage container so as to immerse the entire slide glasses, with samples, in the protection liquid. Therefore, emerging the samples from the protection liquid in the storage container and drying the samples can be securely prevented.

When the slide glass is taken out from the protection liquid in the storage container, the one end side of the slide glass is projected from the protection liquid, and the other side face of the one end side of the slide glass, where no describing portion is formed, is held by the take-out means, so that the slide glass can be taken out from the protection liquid. With this structure, blur of letters or marks caused by contact between the take-out means and the describing portion can be prevented.

By projecting the one end side of the slide glass from the protection liquid, the describing portion of the slide glass is projected from the protection liquid, so that no protection liquid remains on the describing portion.

Therefore, the enclosure agent, which has been dispensed onto the sample applied on the one side face of the slide glass, is not extended to the describing portion, so that the sticking state of the cover glass can be maintained good.

EMBODIMENTS OF THE INVENTION

Figure 1:
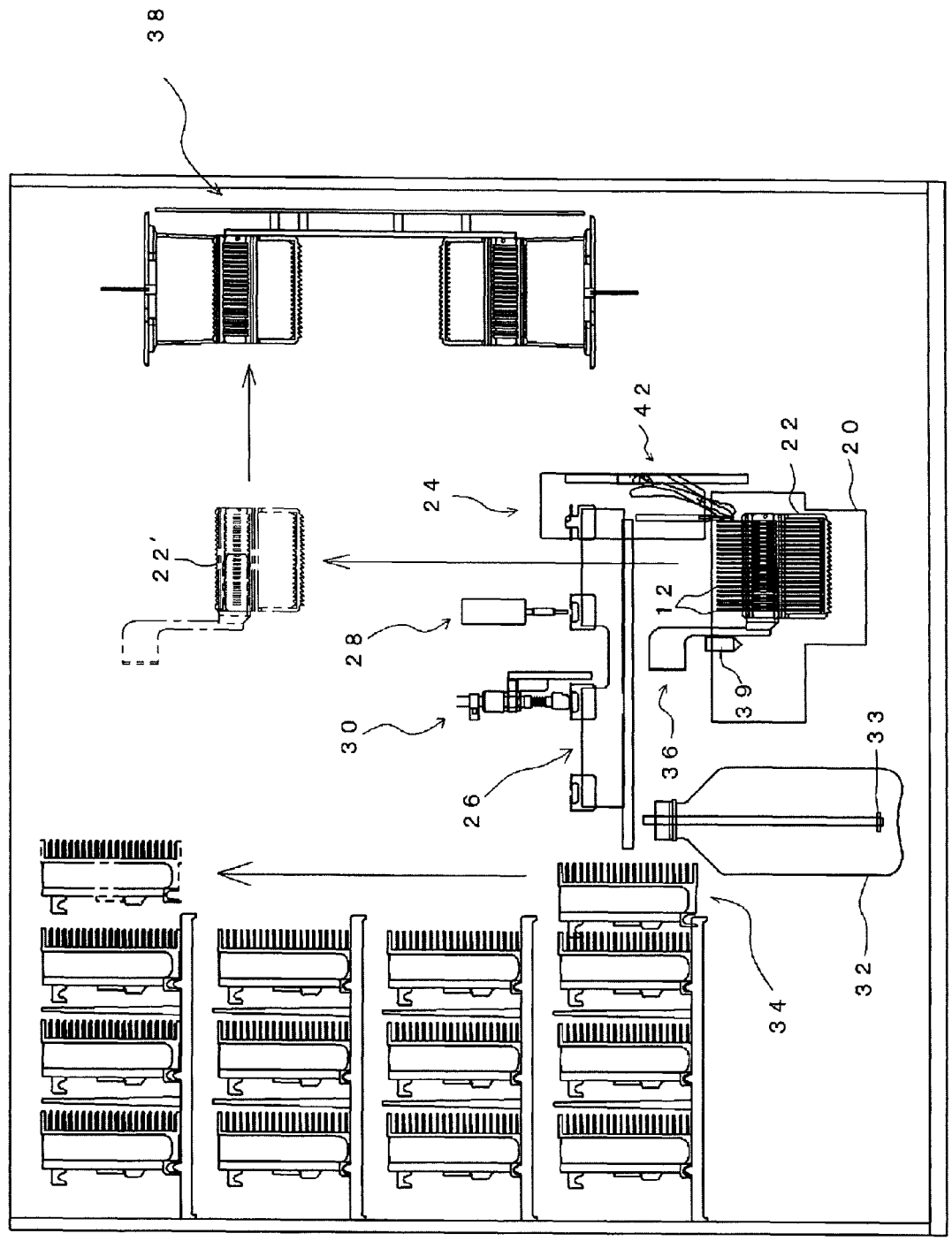
[FIG. 1] It is a schematic front view of an embodiment of the device for sticking a cover glass invented by the inventors of the present invention.
Figure 2:
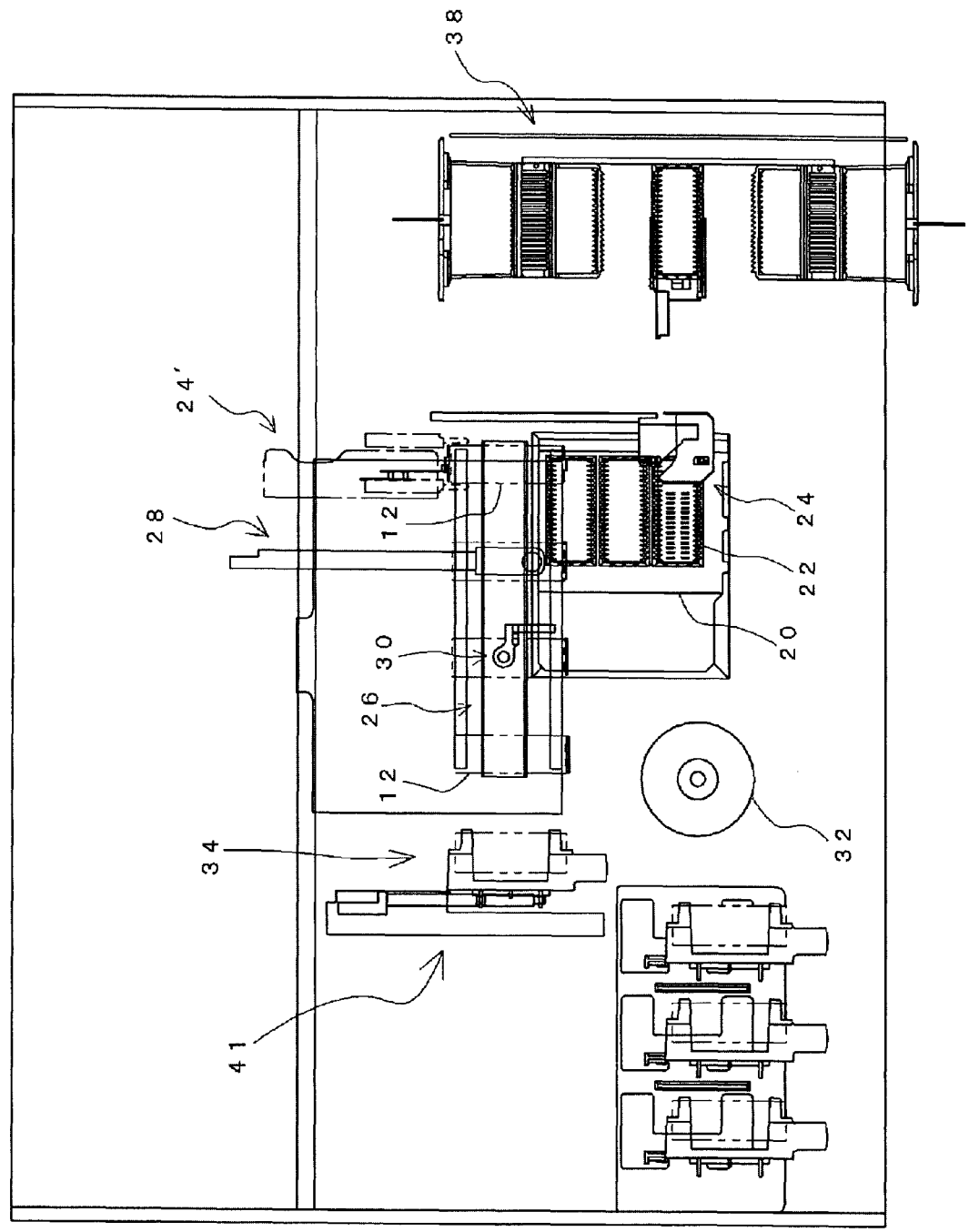
[FIG. 2] It is a schematic plan view of the device shown in FIG. 1.

An embodiment of the cover glass sticking device of the present invention is shown in FIGS. 1 and 2. FIG. 1 is a schematic front view of the device, and FIG. 2 is a schematic plan view of the device.

In the cover glass sticking device shown in FIGS. 1 and 2, a protection liquid, e.g., xylene, is stored in a storage container 20, and a plurality of baskets 22, 22 . . . are inserted in the storage container as shown in FIG. 2. A plurality of slide glasses 12, 12 . . . are accommodated in each of the baskets 22, 22 . . . .

Figure 14:
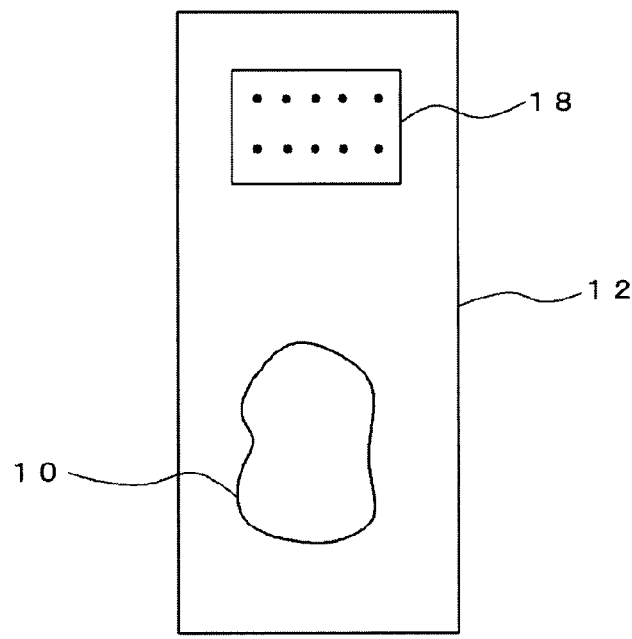
[FIG. 14] It is a front view of the slide glass.
Figure 15:
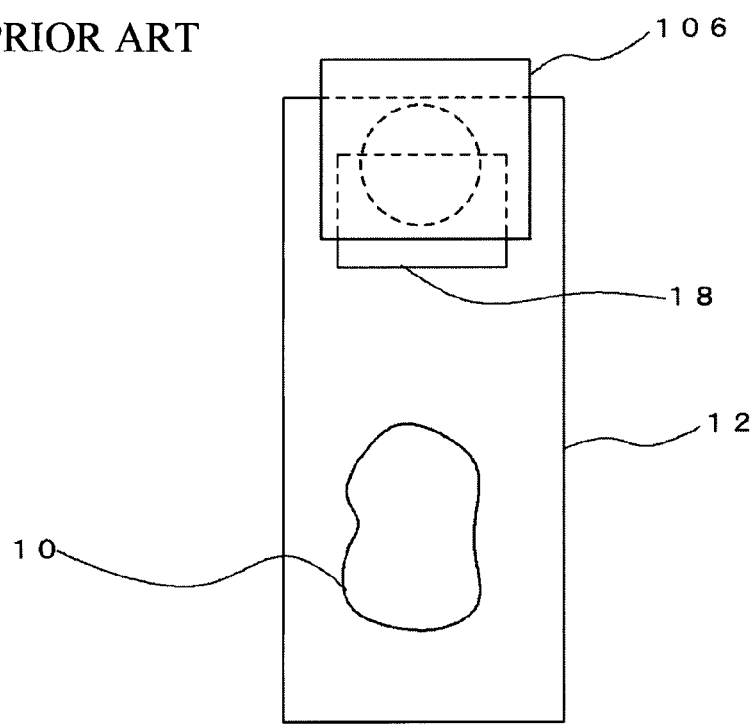
[FIG. 15] It is an explanation view in which the slide glass shown in FIG. 14 is sucked by the sucking member of the conventional device shown in FIG. 12.

In the slide glass 12, as shown in FIG. 14, a sample 10 of microscopic specimen is applied to one end side of the slide glass 12, and a describing portion 18, in which letters or marks for indicating a prescribed item(s) of the sample 10 will be written, is provided thereto. The describing portion 18 may be constituted by a frosted glass plate, on which the letters or marks can be directly written by a pencil, or a label which is adhered by adhesive having resistance to the protection liquid.

One slide glass 12 is taken out, by a take-out unit 24, from the basket 22, in which the plurality of slide glasses 12, 12 . . . are accommodated, and transferred to one end of a conveying unit 26. In the conveying unit 26, the slide glass 12, which has been transferred to the one end, is conveyed toward the other end of the conveying unit 26, and an enclosure agent 14 is dispensed onto the sample 10 of the slide glass 12 at a dispensing position, at which the enclosure agent 14 is dispensed by a dispenser 28. The enclosure agent is supplied from a bottle 32 to the dispenser 28.

In the bottle 32, a level sensor 33 for detecting a level of the enclosure agent is provided in the vicinity of an inner bottom face of the bottle 32. When the level of the enclosure agent is detected by the level sensor 33, supplying the enclosure agent is stopped so as to prevent the enclosure agent from being mixed with air.

The slide glass 12, in which the enclosure agent 14 has been dispensed onto the sample 10 by the dispenser 28, is further conveyed toward the other end of the conveying unit 26 until reaching a cover glass mounting position, at which a cover glass 16 is mounted onto the enclosure agent 14 by a mounting unit 30.

The slide glass 12, on which the cover glass 16 has been mounted, is conveyed to the other end of the conveying unit 26, and then it is inserted into a cage 34.

The vacant basket 22', from which all of the slide glasses 12, 12 . . . have been taken out, is taken out from the storage container 20 and accommodated in a vacant basket accommodating section 38.

Figure 3:
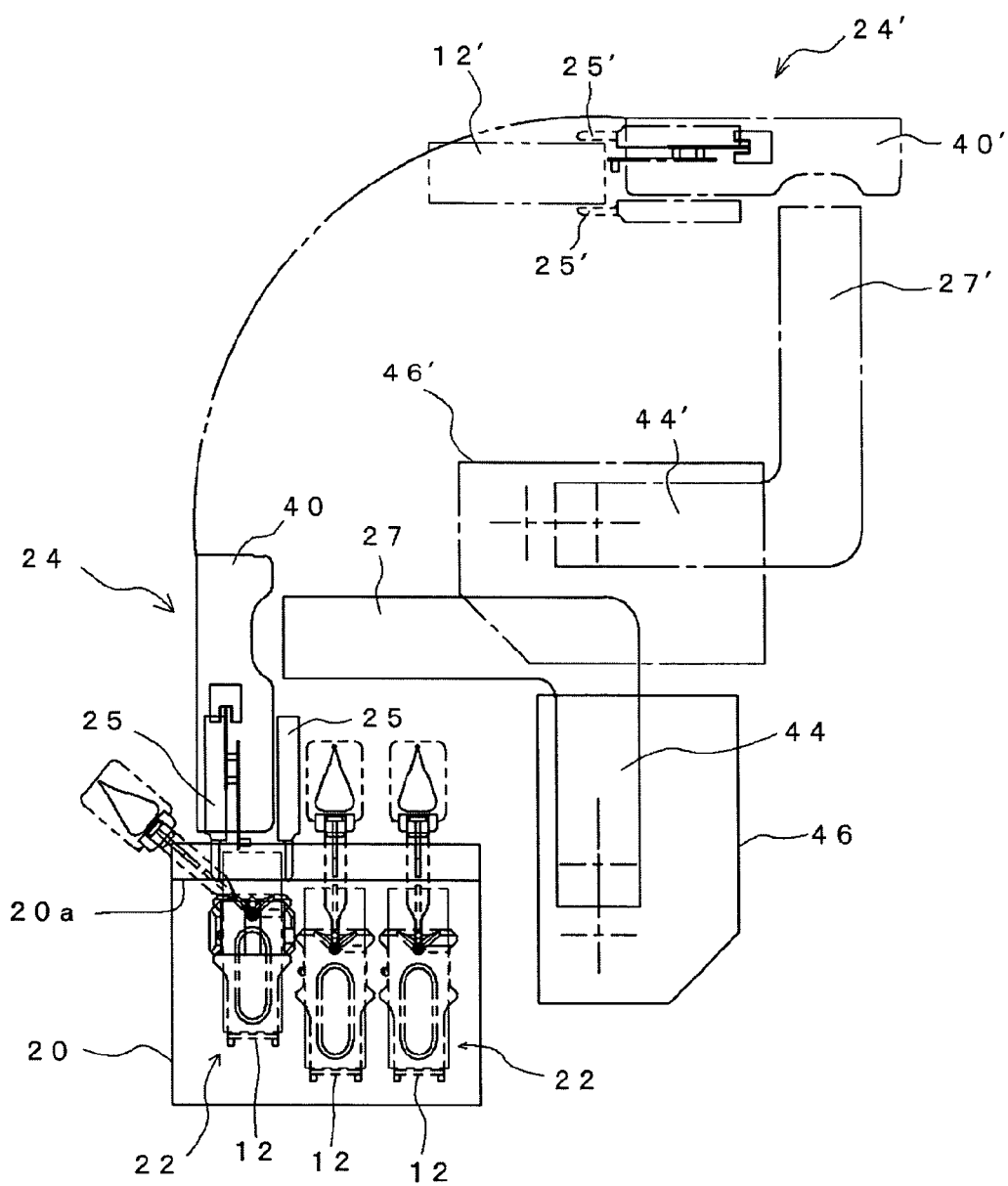
[FIG. 3] It is a schematic view of a take-out unit for taking out a slide glass.

In the storage container 20 of the cover glass sticking device shown in FIGS. 1 and 2, the baskets 22, in each of which the plurality of slide glasses 12 are accommodated, are immersed in the protection liquid as shown in FIG. 3, and the entire slide glasses 12, 12 . . . accommodated in the baskets 22 are also immersed in the protection liquid.

When the slide glasses 12, 12 . . . , which are entirely immersed in the protection liquid, are taken out by the take-out unit 24, the basket 22 is lifted upward, by a lifting unit 36, so as to project one end side of each of the slide glasses 12, 12 . . . from the level 20a of the protection liquid.

Figure 4:
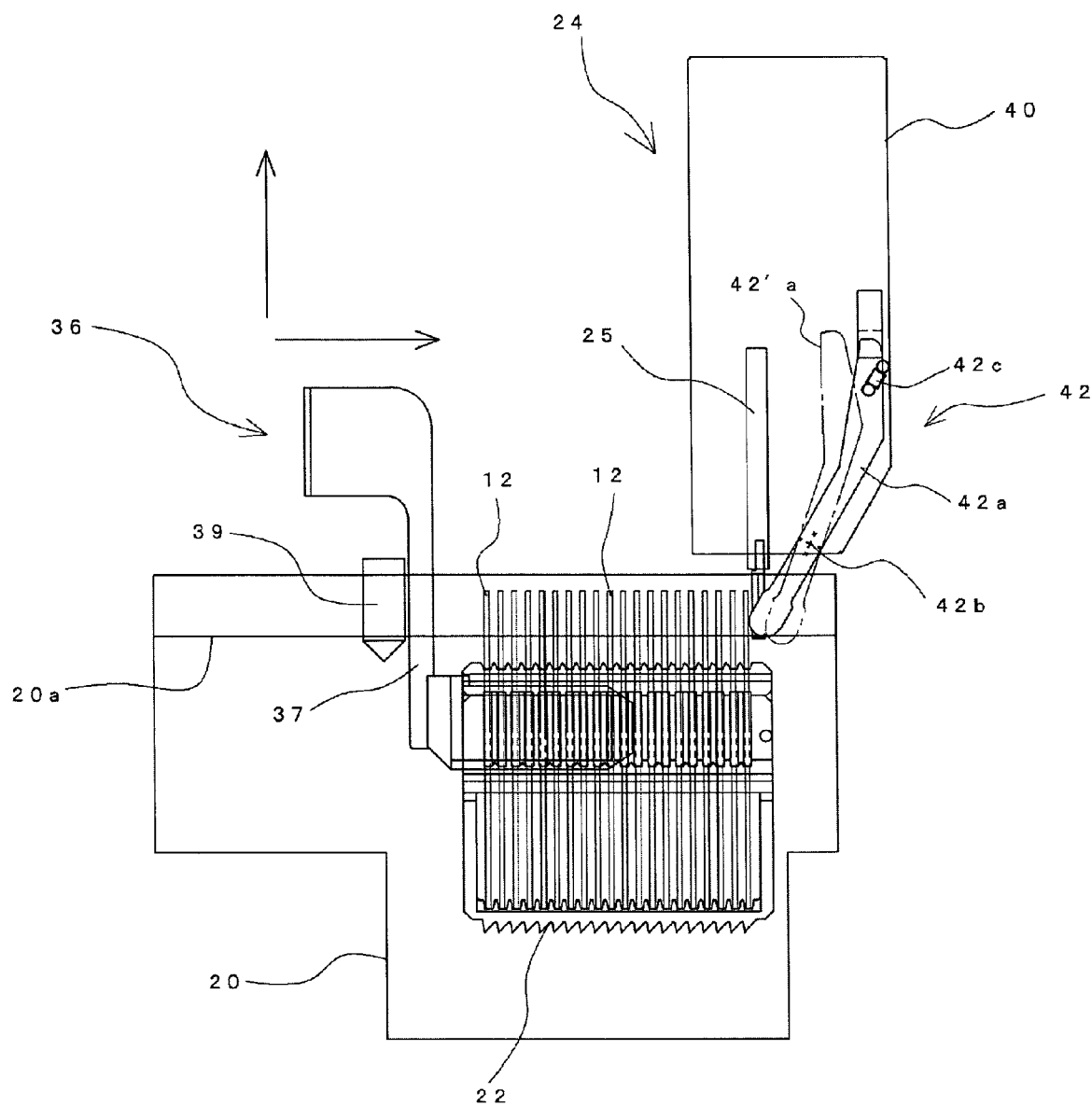
[FIG. 4] It is a schematic view of a lifting unit for lifting a basket and a detection sensor.

As shown in FIG. 4, the basket 22 is lifted by the steps of: holding the basket 22 by a front end of an L-shaped arm 37 of the lifting unit 36; and moving the arm 37 upward. The arm 37 is moved upward, on the basis of the level 20a of the protection liquid detected by the level sensor 33, until the one end side of each of the slide glasses 12, 12 . . . is fully projected from the level 20a.

By projecting the one end side of the slide glass 12 from the protection liquid, the describing portion 18 of the slide glass 12 can be projected from the protection liquid, so that the unnecessary protection liquid can be removed from the describing portion 18. Therefore, extending the enclosure agent, which has been dispensed onto the sample 10, to the describing portion 18 can be prevented.

By using the arm 37, each of the slide glasses 12, 12 . . . , whose one end side is projected from the level 20a of the protection liquid, is taken out, by the take-out unit 24, from the basket 22. As shown in FIG. 3, a side face of the one end side of the slide glass 12, which is projected from the level 20a of the protection liquid, is held, by claw members 25 and 25 of the take-out unit 24, so as to take out the slide glass 12.

Even if the side face of the one end side of the slide glass 12 is held by claw members 25 and 25, the claw members 25 and 25 do not contact the describing portion 18, so that blurring the letters or marks written in the describing portion 18 can be prevented.

The claw members 25 and 25 are provided to one end part 40 of a U-shaped rotary arm 27. The one end part 40 of the arm 27 is capable of independently rotating.

The arm 27 cannot move along the basket 22. In the cover glass sticking device shown in FIGS. 1 and 2, the lifting unit 36 also acts as a unit for feeding the basket 22, so the basket 22 is moved, by an arm 37, toward the claw members 25 and 25.

When the arm 37 moves the basket 22 until the slide glass 12 reaches a prescribed position at which the side face of the slide glass can be held by the claw members 25 and 25, a detection sensor 42, which is provided to the one end part 40 of the arm 27, detects the slide glass.

As shown in FIG. 4, the detection sensor 42 has a bent arm 42a, and the bent arm 42a is capable of rotating, in a vertical plane, about a shaft 42b connected to the one end part 40 of the arm 27. Further, a biasing member, e.g., spring 42c, is connected to the upper end of the arm 42a so as to bias the lower end of the arm 42a toward the one end face of the slide glass 12 which is projected from the level 20a of the protection liquid.

When the lower end of the arm 42a contacts the one end side of the slide glass 12, which is projected from the level 20a of the protection liquid, and the side face of the one end side of the slide glass 12 reaches the prescribed position at which the side face of the slide glass can be held by the claw members 25 and 25, the arm 42a is turned against the biasing force of the spring 42c. When the arm 42a is turned until reaching a position 42'a shown in FIG. 4, the movement of the arm 37 toward the claw members 25 and 25 is stopped, and the claw members 25 and 25 hold the side face of the one end side of the slide glass 12.

As shown in FIG. 3, the U-shaped arm 27, which includes the claw members 25 and 25 holding the side face of the one end side of the slide glass 12, has the other end part 44 which is fixed to a rotatable section 46. With this structure, as shown in FIG. 3, the one end part 40 of the arm 27 is turned 90° by turning the rotatable section 46 90°, so that the slide glass 12 immersed in the protection liquid, which is stored in the storage container 20, can be taken out and disposed parallel to the level 20a of the protection liquid. (A sample application face of the slide glass 12, on which the sample 10 is applied, is vertically disposed with respect to the level 20a of the protection liquid.)

The one end part 40 having the claw members 25 and 25 is also rotatable. Therefore, the one end part 40 is turned so as to face up the sample application face of the slide glass 12, on which the sample 10 is applied, and then the slide glass is transferred to the one end of the conveying unit 26 as shown in FIGS. 1 and 2.

Figure 5:
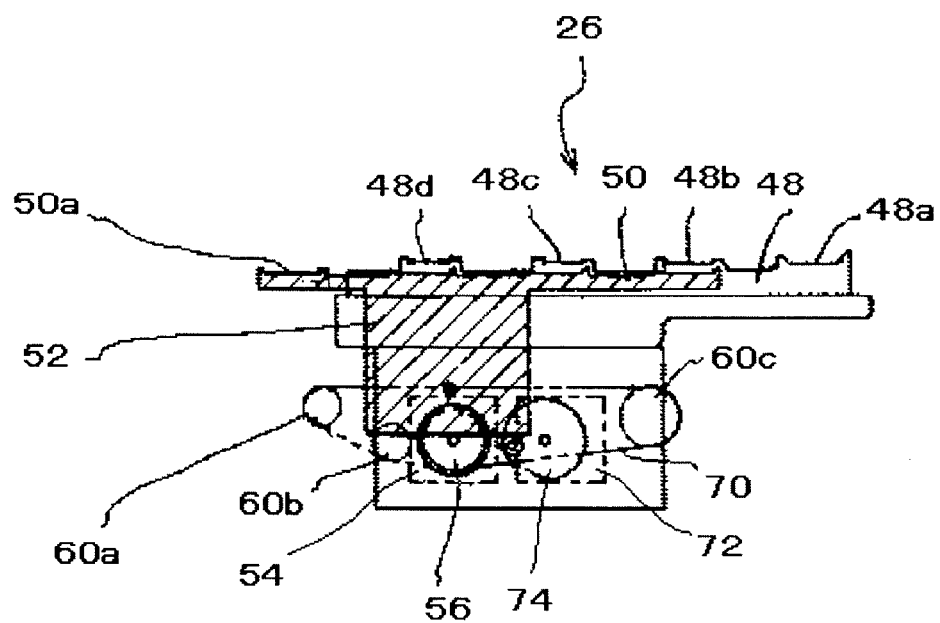
[FIG. 5] It is a schematic view of a conveying unit for conveying the slide glass.

The conveying unit 26 is shown in FIG. 5. The conveying unit 26 shown in FIG. 5 has a supporting member 48, and the supporting member 48 has a plurality of concave parts for supporting the both ends of the slide glass 12 which has taken out in the horizontal state. A first concave part 48a, a second concave part 48b, a third concave part 48c and a fourth concave part 48d are serially formed from the take-out unit 24 side.

The slide glass 12 which has been taken out from the storage container 20 and put on the first concave part 48a is sequentially conveyed to the second concave part 48b, the third concave part 48c and the fourth concave part 48d by a conveying plate 50.

In an upper face of the conveying plate 50, a plurality of concave parts 50a are formed, side by side, from one end, which is located on the take-out unit 24 side, to the other end, and a projected section 52 is downwardly projected from a bottom of the conveying plate.

The projected section 52 is engaged with a belt 70, which is engaged with a driving pulley 56 driven by a motor 54 and driven pulleys 60a, 60b and 60c, and moved upward and downward by a cum 74 driven by a motor 72. Therefore, the conveying plate 50 can be moved upward at a prescribed position, horizontally moved in a prescribed direction, and then moved downward at another prescribed position and horizontally moved in the opposite direction. When the slide glass 12 supported by the first concave part 48a of the supporting member 48 of the conveying unit 26 is conveyed to the second concave part 48b, the dispenser 28 dispenses the enclosure agent 14 onto the sample 10 applied to the slide glass 12.

Figure 6:
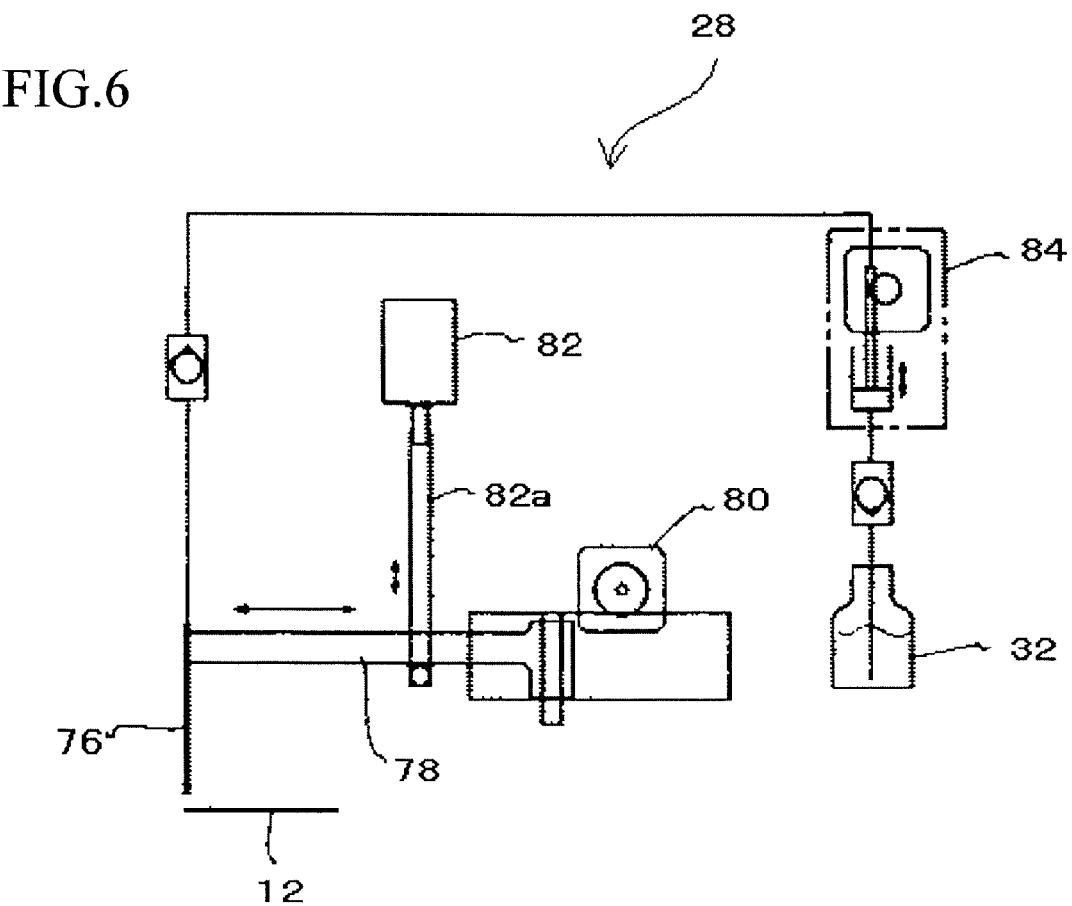
[FIG. 6] It is a schematic view of a dispenser.
Figure 7:
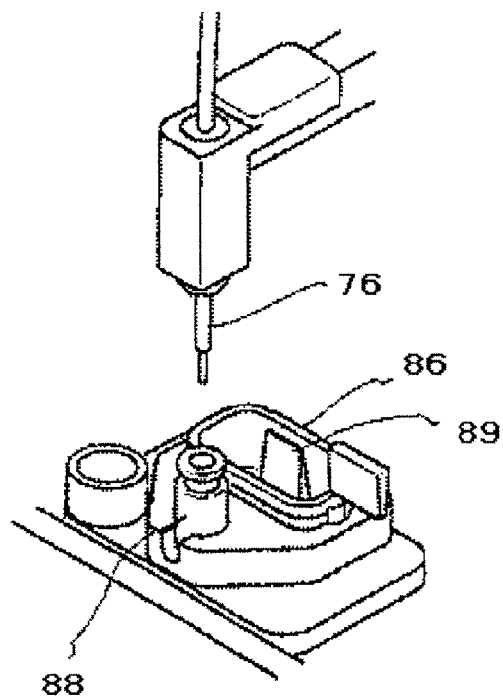
[FIG. 7] It is a partial perspective view of the dispenser.

In the dispenser 28, as shown in FIG. 6, one end of a connecting member 78 is connected to a dispensing nozzle 78; the other end of the connecting member is connected to a motor 80, which constitutes a sliding unit for horizontally moving the dispensing nozzle 76; and a rod 82a of a solenoid 82, which constitutes an elevating unit for vertically moving the dispensing nozzle 78, is connected to a mid part of the connecting member 78.

With this structure, the dispensing nozzle 76 can be moved in the vertical direction and the horizontal direction. The enclosure agent stored in the bottle 32 is supplied to the dispensing nozzle 76 by a plunger pump 84 which acts as a constant liquid supplying unit.

As shown in FIG. 1, the level sensor 33 is provided in the vicinity of the inner bottom face of the bottle 32, so supplying the enclosure agent by the plunger pump 84 is stopped so as to prevent the enclosure agent from being mixed with air when the level of the enclosure agent in the bottle 32 is detected by the level sensor 33.

By employing the dispenser 28, the dispensing nozzle 76 is capable of dispensing the enclosure agent with moving the slide glass 12, which is held in the horizontal state, in the longitudinal direction thereof. Further, the plunger pump 84 is capable of constantly dispensing the enclosure agent, so that variation of the amount of enclosure agent can be restrained.

The dispensing nozzle 76 is capable of horizontally moving beyond the longitudinal edge of the slide glass 12, and a waste liquid tray 86 and a container 88, which stores a solvent for preventing the enclosure agent from solidification, are located at prescribed positions, which are located outside of the slide glass 12 and included in a movable range of the dispensing nozzle 76. A removing plate 89 is extended upward from the waste liquid tray 86 so as to remove the enclosure agent drooping from the front end of the dispensing nozzle 76.

The slide glass 12, which is held in the second concave part 48b of the supporting member 48 of the conveying unit 26 and in which the enclosure agent has been dispensed onto the sample 10, is transferred to the third concave part 48c, and then the cover glass 16 is mounted onto the enclosure agent 14 by the mounting unit 30.

Figure 8:
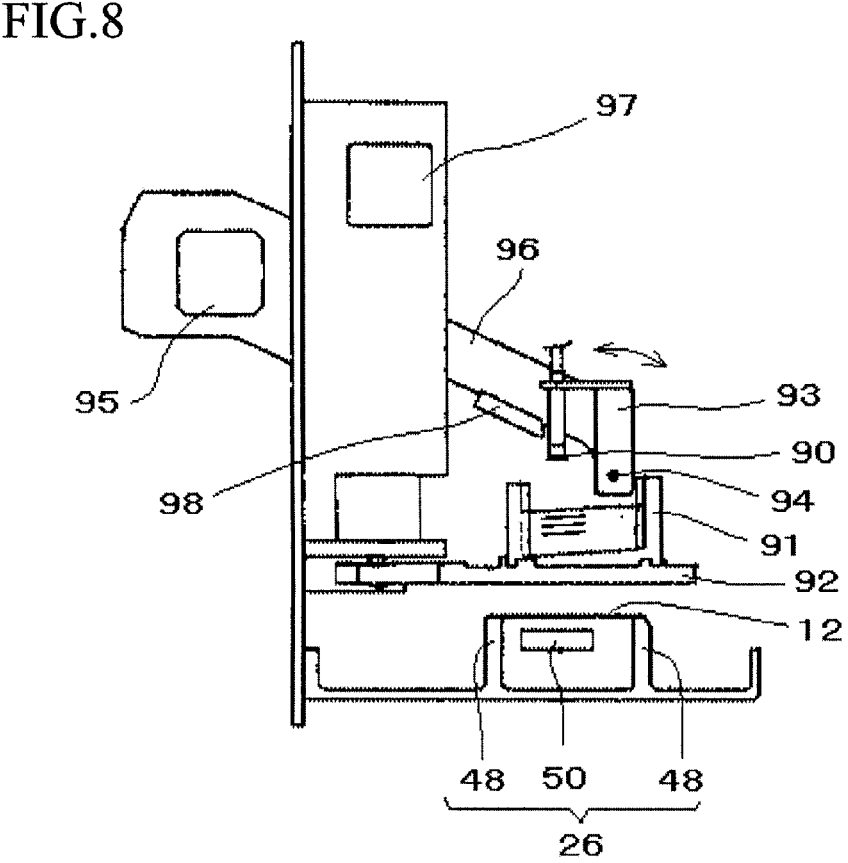
[FIG. 8] It is a schematic view of a cover glass mounting unit.

As shown in FIG. 8, the mounting unit 30 has a sucking pad 90 for sucking and holding the cover glass, and a holder 90 for accommodating the plurality of cover glasses in a stacked state. The holder 91 is mounted on a holder table 92, which is rotatable in a horizontal plane above the conveying unit 26. The plurality of cover glasses are obliquely stacked in the holder 91, and the sucking pad 90, which acts as holding means, takes out the uppermost cover glass 16 of the stacked cover glasses from the holder 91. The sucking pad 90 is provided to one end of an arm 93. A motor 95 rotates the arm 93 about a shaft 94 which is located at the other end of the arm, and a motor 97 moves an arm holding member 96, to which the arm 93 is attached, upward and downward. Further, in the arm holding member 96, a pin 98 is provided in the vicinity of the sucking pad 90.

Figure 9:
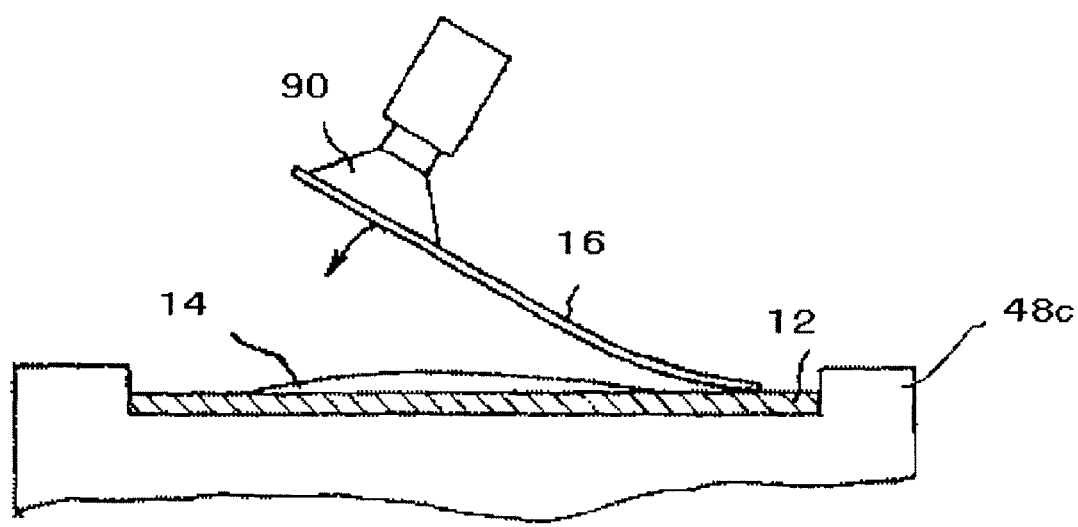
[FIG. 9] It is an explanation view showing a manner for mounting a cover glass onto the slide glass.

By employing the mounting unit 30 shown in FIG. 8, the arm 93 is turned so as to bring the cover glass 16 into contact with the enclosure agent 14, which has been dispensed onto the sample 10 of the slide glass 12 held in the third concave part 48b, from one longitudinal end of the cover glass 16 to the other longitudinal end thereof gradually, as shown in FIG. 9. In this action, a turning speed of the arm 93 can be adjusted by adjusting a rotational speed of the motor 95. After the one longitudinal end of the cover glass 16 contacts the enclosure agent, the rotational speed of the motor 95 may be controlled to gradually reduce or increase the turning speed of the arm 93, according to properties of the enclosure agent, a dispensing speed, etc., so as to easily purge air from the space between the cover glass 16 and the slide glass 12.

The slide glass 12, on which the cover glass 16 has been mounted, is transferred to the fourth concave part 48d of the supporting member 48 of the conveying unit 26 and inserted into the cage 34 in order.

To sequentially insert the slide glasses 12 at prescribed positions of the cage 34, an inserting position of the cage, at which the slide glass 12 on which the cover glass 16 has been mounted is inserted, is adjusted, by a lift 41, for moving the cage 34 upward and downward as shown in FIG. 2.

The cage 34 corresponds to the basket 22 from which the slide glass 12 is being taken out by the take-out unit 24, the cage 34 is moved upward and transferred to an initial position or an empty position at which no cage 34 is set, after all of the slide glasses 12 is conveyed from the basket 22 to the cage 34, and then a position of the next cage 34 is regarded as the inserting position, at which the slide glass 12 will be inserted.

When the all of the slide glasses 12 are taken out from the basket 22 which is inserted in the storage container 20, the L-shaped arm 37 of the lifting unit 36 is moved upward, as shown in FIG. 1, so as to accommodate the vacant basket 22 in the vacant basket accommodating section 38, which is located in the vicinity of the take-out unit 24.

Figure 10:
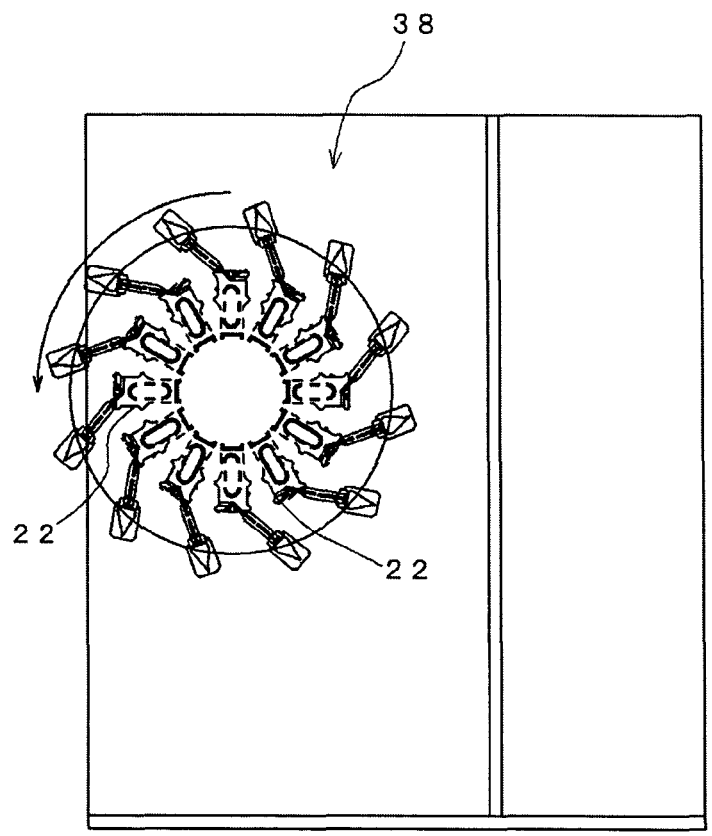
[FIG. 10] It is an explanation view of a vacant basket accommodating section.
Figure 11:
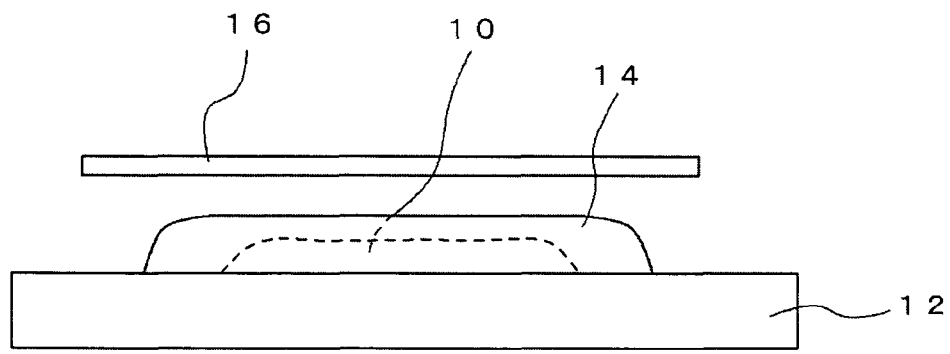
[FIG. 11] It is an explanation view showing a manner for producing a microscopic specimen.
Figure 12:
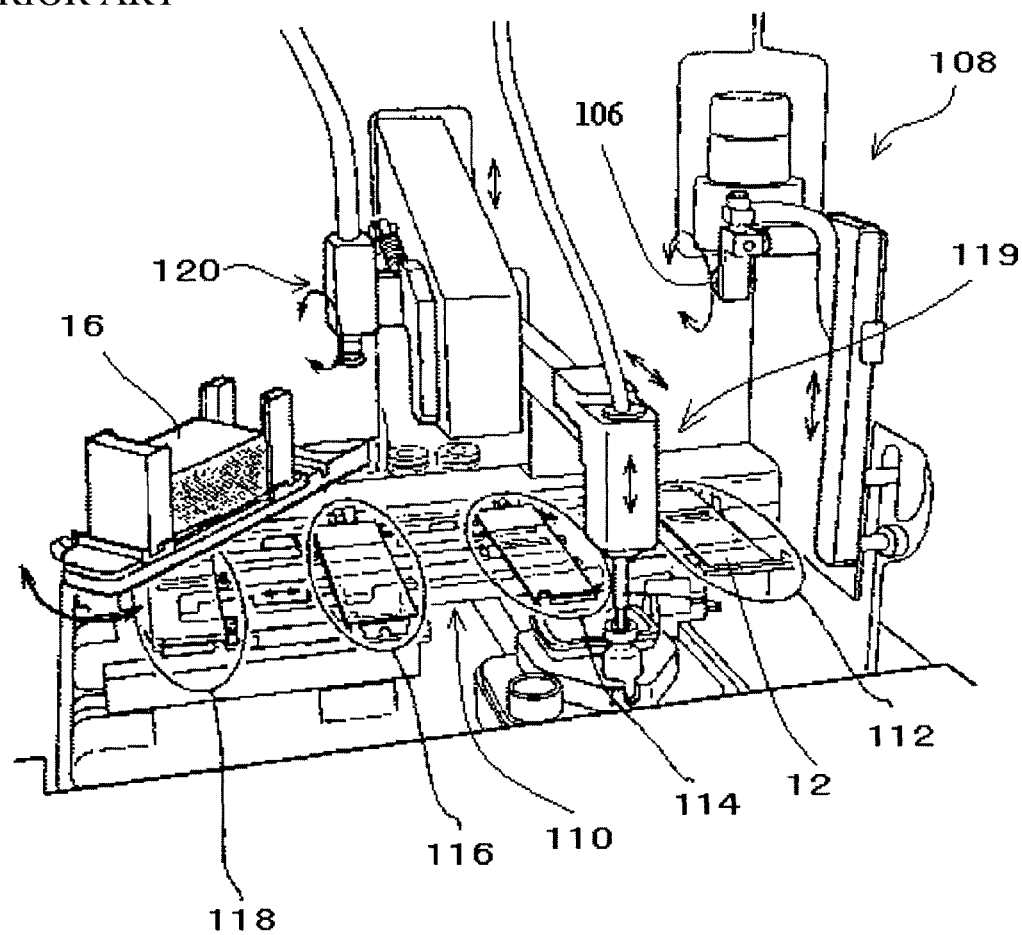
[FIG. 12] It is a partial perspective view of the conventional cover glass sticking device.
Figure 13:
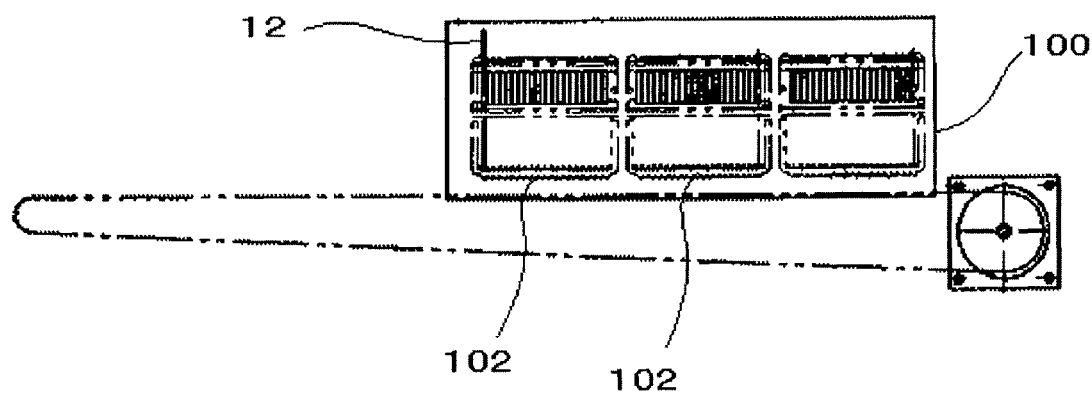
[FIG. 13] It is an explanation view of the storage container included in the conventional device shown in FIG. 12.

As shown in FIG. 10, when the vacant basket accommodating section 38 is filled with the vacant baskets 22, 22 . . . , the vacant basket accommodating section 38 can be detached from the main body section of the device and the vacant baskets 22, 22 . . . can be taken out therefrom.

What is claimed is:

1. A device for sticking a cover glass to a sample of microscopic specimen applied to a slide glass having one end side, where a describing portion is formed on one side face, with an enclosure agent, said device comprising:
    a storage container for immersing a basket, into which a plurality of slide glasses are configured to be inserted, in a protection liquid, which is stored in the storage container and which protects samples of microscopic specimen applied on the slide glasses in the basket, so as to immerse the entire slide glasses therein;
    means for lifting the basket to project one end side of a slide glass from the level of the protection liquid;
    a rotatable arm;
    a detection sensor for detecting a position of one end side of the slide glass projected from the protection liquid, the detection sensor being provided to the arm;
    means for feeding the basket sequentially to a position of the detection sensor;
    two claw members, which are provided to the arm and configured to hold a side face of one end side of the slide glass detected by the detection sensor, the two claw members for taking out the slide glass from the protection liquid by rotating the arm; and
    a cage for containing the slide glass, on which the cover glass has been stuck to cover the sample.

2. The device according to claim 1, further comprising means for conveying a vacant basket, from which all of the slide glasses have been taken out, to a vacant basket accommodating section.

3. The device according to claim 1, wherein the plurality of cages are used, and the slide glasses in one basket are contained in the same cage.

4. The device according to claim 2, wherein the plurality of cages are used, and the slide glasses in one basket are contained in the same cage.

5. The device according to claim 1, wherein the lifting means and the feeding means are integrated.

6. The device according to claim 2, wherein the lifting means and the feeding means are integrated.

7. The device according to claim 3, wherein the lifting means and the feeding means are integrated.

8. The device according to claim 4, wherein the lifting means and the feeding means are integrated.

* * * * *